(12) United States Patent
Alaoui-Jamali et al.

(10) Patent No.: US 7,094,891 B1
(45) Date of Patent: Aug. 22, 2006

(54) REPLICATION PROTEIN A BINDING TRANSCRIPTIONAL FACTOR (RBT1) AND USES THEREOF

(75) Inventors: Moulay A. Alaoui-Jamali, Laval (CA); John Myung-Jae Cho, Westmount (CA)

(73) Assignee: Center for Translation Research in cancer, Montreal (CA)

( * ) Notice: Subject to any disclaimer, the term of this patent is extended or adjusted under 35 U.S.C. 154(b) by 235 days.

(21) Appl. No.: 10/069,386

(22) PCT Filed: Aug. 17, 2000

(86) PCT No.: PCT/CA00/00948

§ 371 (c)(1),
(2), (4) Date: Sep. 12, 2002

(87) PCT Pub. No.: WO01/14546

PCT Pub. Date: Mar. 1, 2001

Related U.S. Application Data

(60) Provisional application No. 60/149,472, filed on Aug. 19, 1999.

(51) Int. Cl.
- *C07H 21/00* (2006.01)
- *C07K 14/00* (2006.01)
- *C12N 15/83* (2006.01)
- *C12N 15/86* (2006.01)

(52) U.S. Cl. .................. 536/23.5; 435/455; 530/350
(58) Field of Classification Search ................ 536/23.1, 536/23.5; 530/350; 424/93.2; 435/455, 435/320.1
See application file for complete search history.

(56) References Cited

FOREIGN PATENT DOCUMENTS

| WO | WO98/00013 A | 1/1998 |
| WO | WO98/37901 A | 9/1998 |

OTHER PUBLICATIONS

Gerhold et al. BioEssays, 18:973-981, 1996.*
Attwood, Science 290:471-473, 2000.*
Singh et al. (1995), "," 92 *Proceedings of the National Academy of Science USA* 11:4907-4911.
Hillier et al. (1997), "zt34d02.r1 Soares Ovary Tumor NbHOT Homo sapiens cDNA Clone IMAGE : 724227 5', mRNA Sequence," Database EM_EST 'Online! EMBL; ID HS1272698, AC AA482412 98.5% nt seq idenity with SEQ ID No.: 1 in 495 nt overlap (14-506 : 60-554).
Marra et al. (1997), "vt32d01.r1 Barstead Mouse Proximal Colon MPLRB6 Mus Musculus cDNA Clone IMAGE: 1164769 5', mRNA Sequence" Database EM_EST 'Online! EMBL; ID AA690874 81.3% nt seq identity with SEQ ID No.: 1 in 402 nt overlap (9-410 : 190-591).
Nagelhus et al. (1997), "A Sequence in the N-Terminal Region of Human Uracil-DNA Glycosylase with Homology to XPA Interacts with the C-Terminal Part of the 34-kDa Subunit of Replication Protein A," 272 *Journal of Biological Chemistry*, 10:6561-6566.
Wold (1997), "Replication Protein A: A Heterotrimeric, Single-Stranded DNA-binding Protein Required for Eukaryotic DNA Metabolism," 66 *Annual Review of Biochemistry* 61-92 XP001002023 cited in the applicaton abstract p. 74, line 17 -p. 76, line 27.
Hays et al. (1998), "," 18 *Molecular and Cellular Biology* 7:4400-4406.
Iftode et al. (1999), "Replication Protein A (RPA): the Eukaryotic SSB," 34 *Critical Reviews in Biochemistry and Molecular Biology* 3:141-180, XP001002021 abstract figure 1 p. 159, left-hand col., line 34 -p. 166, left-hand col., line 29; table 2.
Database EM_HUM 'Online! EMBL ID AC010271 (1999) "Homo sapiens Chromosome 19 CTC-492K19, Complete Sequence," Doe Joint Genome Institute Stanford Human Genome Center XP002167207 99.8% nt seq identity with SEQ ID No.: 1 in 591 nt overlap (23191-23781:1-591) p. 6-7.
Cho et al. (2000), "RBT1, a Novel Transcriptional Co-activator, Binds the Second Subunit of Replication Protein A," 28 *Nucleic Acids Research* 18:3478-3485 XP002167204 the whole document.

* cited by examiner

*Primary Examiner*—Brian Whiteman
(74) *Attorney, Agent, or Firm*—Keown & Associates

(57) ABSTRACT

The present invention relates to replication protein A (RPA) transcriptional factors. There is provided a nucleotide sequence encoding a replication protein A transcriptional activator 1 (RTB1) and a protein encoded by such a nucleotide sequence. RBT1 has a high activity and is highly transactivated in cancer cells. The sequence may be used to treat neoplastic disorders and in gene therapy.

4 Claims, 1 Drawing Sheet atggagggaggcttgaagaggaaacactctgatttggaagaggaggaggagaggtgggag
M   E   G   G   L   K   R   K   H   S   D   L   E   E   E   E   R   W   E
1                                                                       20 tggagtccagcaggccttcagagctaccagcaagccctgctccgcatctccctagacaaa
W   S   P   A   G   L   Q   S   Y   Q   Q   A   L   L   R   I   S   L   D   K
21                                                                      40 gtccagcgcagcctgggccccgagcacccagcctccgcaggcatgtcctcatccataac
V   Q   R   S   L   G   P   R   A   P   S   L   R   R   H   V   L   I   H   N
41                                                                      60 accctccaacagctgcaggctgcacttcgcctggctcccgcccctgccctgccccccgag
T   L   Q   Q   L   Q   A   A   L   R   L   A   P   A   P   A   L   P   P   E
61                                                                      80 cccctcttcctgggcgaggaggatttctccctgtcagccaccattggctctatcctcagg
P   L   F   L   G   E   E   D   F   S   L   S   A   T   I   G   S   I   L   R
81                                                                     100 gagctggacacctccatggatgggactgagccccctcagaatccagtgactccccttggc
E   L   D   T   S   M   D   G   T   E   P   P   Q   N   P   V   T   P   L   G
101                                                                    120 ctccagaatgaagtgccaccccagcctgatccagtcttcttagaagctctgagctcccgg
L   Q   N   E   V   P   P   Q   P   D   P   V   F   L   E   A   L   S   S   R
121                                                                    140 tacttgggggactctggcctggatgacttctttctggacattgacacatctgcggtagaa
Y   L   G   D   S   G   L   D   D   F   F   L   D   I   D   T   S   A   V   E
141                                                                    160 aaggagcctgcacgggccccaccagagcctcctcacaacctcttctgtgccccaggttct
K   E   P   A   R   A   P   P   E   P   P   H   N   L   F   C   A   P   G   S
161                                                                    180 tgggagtggaatgaactggatcacatcatggaaatcattctggggtcctaa       SEQ ID NO:1
W   E   W   N   E   L   D   H   I   M   E   I   I   L   G   S   Stop   SEQ ID NO:2
181                                              196

FIG. 1

REPLICATION PROTEIN A BINDING TRANSCRIPTIONAL FACTOR (RBT1) AND USES THEREOF

CROSS-REFERENCE TO RELATED APPLICATIONS

This application claims priority to International Application PCT/CA00/00948 filed Aug. 17, 2000 and designating the United States, now abandoned, which claims the benefit of U.S. Provisional Application Ser. No. 60/149,472, filed Aug. 19, 1999; the entire contents of which are hereby incorporated by reference.

BACKGROUND OF THE INVENTION (a) Field of the Invention

The invention relates to Replication Protein A (RPA) and more particularly to a RPA transcriptional factor to treat neoplastic disorders such as cancer.

(b) Description of Prior Art

Replication Protein A (RPA), also known as replication factor A (RFA), is a ubiquitous and abundant heterotrimeric protein required for DNA replication, repair and recombination in eukaryotes. RPA nonspecifically binds single-stranded DNA and plays an essential role in the regulation of DNA metabolism via multiple protein interactions and/or RPA phosphorylation. More particularly, RPA binds single-stranded DNA with strong affinity (association constant of $10^9$–$10^{11}$ $M^{-1}$) and greatest affinity for polypyrimidine tracts. RPA also binds double-stranded DNA with lower affinity and is likely to facilitate DNA unwinding. RPA may play a role in the regulation of transcription by binding regulatory elements in promoters; in yeast, RPA binds specific regulatory sequences in the promoters of DNA repair and metabolism genes (Singh K. et al., 1995, *Proceedings of the National Academy of Science USA* 92(11): 4907–11).

RPA is made of three subunits: a 70-kDa subunit (RPA70), a 32-kDa middle subunit (RPA32) and a 14-kDa subunit (RPA14). The RPA32 subunit is phosphorylated in a cell cycle-dependent manner.

RPA-protein interactions appear to be largely mediated by the large 70-kDa subunit (RPA70). RPA70 interacts with the p53, GAL4, VP16, EBNA1 and SV40T antigens and with DNA polymerase alpha (Wold, M., 1997, *Annual Review of Biochemistry*, "Replication Protein A: A Heterotrimeric, Single-Stranded DNA-binding Protein Required for Eukaryotic DNA Metabolism"). It is also important in interaction with DNA repair proteins involved in damage recognition and excision.

Interaction with XPF stimulates its 5' junction-specific endonuclease activity, interaction with XPG targets this endonuclease to damaged DNA, and interaction with ERCC1 (ERCC1 also binds *xeroderma pigmentosum* group A factor, XPA, which is another NER factor) promotes exonuclease activity.

The possibility of interaction by the aforementioned repair proteins with RPA32 has not been clearly elucidated. However, interactions with some proteins involved in DNA repair appear to be mediated by RPA32, such as interaction with XPA and uracil-DNA glycosylase. A region of significant homology between uracil-DNA glycosylase and XPA was also reported, suggestive of the possibility of a common binding motif to RPA32 across several different proteins. Furthermore, some important protein interactions, such as with RAD52, appear to involve all three subunits of RPA (Hays, S. et al., 1998, *Molecular and Cellular Biology* 18(7):4400–4406).

In cells, RPA is phosphorylated by DNA-dependent protein kinase (DNA-PK) when RPA is bound to single-strand DNA, during the S phase and after DNA damage; and also possibly by ATM.

Phosphorylation of RPA is observed in a cell-cycle dependent manner and in response to DNA damage (i.e. UV light, X-rays, cisplatin) in eukaryotic systems. This phosphorylation takes place predominantly on the N-terminal region of RPA32 and was previously thought to be effected by DNA-dependent protein kinase (DNA-PK). However, RPA hyperphosphorylation still takes place in SCID cells where DNA-PK is believed to be responsible for its repair and recombination defects. Ataxia telangiectasia mutated gene (ATM), an important cell cycle checkpoint protein kinase belonging to the same kinase family as DNA-PK, may be responsible for the in vivo phosphorylation of RPA32. In *Saccharomyces cerevisiae*, the ATM homolog, MEC1, is essential for RPA phosphorylation. Furthermore, ionizing radiation-induced phosphorylation of RPA32 is deficient and reduced in primary fibroblasts from patients suffering from ataxia telangiectasia in comparison to normal, aged fibroblasts.

The result of RPA32 phosphorylation on DNA metabolism is largely unsolved. It has been noted that IR-induced RPA phosphorylation can be uncoupled from the S-phase checkpoint in ataxia telangiectasia cells, suggesting that RPA phosphorylation in itself is not necessary or sufficient for an S-phase arrest. Phosphorylation, however, may affect the conformation of RPA, thereby modulating its affinity for DNA and its protein interactors, and altering the balance between DNA replication and repair. Hyperphosphorylation of RPA32 in vivo is concordant with a decrease in the binding of RPA to single-stranded DNA. This observation is interesting to note since phosphorylated RPA32 is found predominantly in the S-phase of the cell cycle.

RPA has been found to have a high affinity for UV-damaged and cisplatin-damaged DNA and the accompanying phosphorylated form of RPA is correlated strongly with a reduction of the in vitro DNA replication activity of the concerned cell extracts.

It would therefore be highly desirable to identify physiologically relevant protein interactors of the RPA32 subunit of Replication Protein A. Identification of such protein interactors would contribute to the understanding of DNA repair, transcription, and cell signaling. The proteins involved in nucleotide excision repair (NER), for example, are quite numerous and the basis for their interaction and function is not yet completely understood. Understanding the regulation of these pathways would assuredly lend insight into their role in cancer susceptibility. RPA, as a protein involved integrally in modulating DNA repair, replication and recombination, would be key to understanding the connection between and within pathways. The implications to cancer therapeutics and/or prevention would be significant.

SUMMARY OF THE INVENTION

One aim of the present invention is to provide a protein interactor of the RPA32 subunit of Replication Protein A (RPA).

Another aim of the present invention is to provide a RPA transcriptional factor to treat neoplastic disorders such as cancer.

In accordance with the present invention, there is provided a gene having the characteristics of a gene encoded by a nucleotide sequence as set forth in FIG. 1 (SEQ ID NO:1).

The gene may be from a human, a mouse, a rat or a yeast.

In accordance with the present invention, there is also provided a protein having the identifying characteristics of a protein encoded by a nucleotide sequence as set forth in FIG. 1 (SEQ ID NO:1).

The protein may be from a human, a mouse, a rat or a yeast.

Antibodies may be raised against the gene.

The gene, replication protein A binding transcriptional activator 1 (RBT1), encodes a protein interactor of the Replication Protein A (RPA) More particularly, a protein interactor of the Replication Protein A 32KD subunit was identified. RBT1 binds RPA32.

The RBT1 gene has a high activity in cancer cells compared to normal cells, may be involved in carcinogenesis and is highly transactivated in cancer cells.

The RBT1 nucleotide and/or amino acid sequences may be used to generate reagents, such as plasmids, antibodies and inhibitors, including antisense/antibodies which may be used in treating neoplastic disorders such as cancer.

The RBT1 sequence of the present invention may also be used for the preparation of a medicament for gene therapy, wherein he RBT1 sequence is used as a specific promoter to overexpress genes of interest in specific tissues.

In accordance with another embodiment of the present invention, there is provided a method of gene therapy, which comprises the use of RBT1 sequence as a promoter for overexpressing a gene in a suitable tissue.

The RBT1 gene may further be used to induce apoptosis in cells such as cancerous cells, by modulating its expression using molecular or chemical approaches.

The RBT1 sequence of the present invention may also be used to develop antisenses and/or inhibitors to treat diseases including cancers and leukemia.

BRIEF DESCRIPTION OF THE DRAWING

FIG. 1 illustrates the nucleotide (SEQ ID NO:1) and the amino acid sequence (SEQ ID NO:2) of RBT1.

DETAILED DESCRIPTION OF THE INVENTION

In accordance with the present invention, there is provided a gene sequence encoding a protein interactor of Replication Protein A, identified using the yeast two-hybrid system. The gene, named RPA Binding Transcriptional Activator 1 (RBT1), has a putative open reading frame of 196 amino acids. The coding sequence of RBT1 corresponds to several expressed sequence tags (ESTs), including one derived from an ovary tumor cell line. The gene of the present invention acts as a strong transcriptional activator in yeast and mammalian cells. Furthermore, transcriptional activation, as assayed by a luciferase reporter gene, demonstrated that the activity of the RBT1 gene of the present invention is higher in cancer cells compared to normal non-immortalized cells. RBT1 expression is higher in cancer cells compared to normal cells. More particularly, a protein interactor of Human Replication Protein A 32 (RPA32) was identified.

BLASTP homology searches against the deduced amino acid sequence of RBT1 reveal that it is an undefined protein with little homology to known protein sequences. Further, BLASTN homology searches only identified approximately 20 human expressed sequence tags (ESTS) which had high homology to RBT1.

Northern blot using an RBT1 DNA probe showed one transcript of approximately 1.55 kb in size. In silico analysis suggested that RBT1 consists of an open reading frame (ORF) of 196 amino acids and a theoretical molecular weight of 22 kDa. This is in agreement with Western Blot analysis.

Differential expression of RBT1 was also investigated as it relates to cancer. Semi-quantitative analysis has shown that RBT1 is at least ten times more expressed in cell line H661 (cancer cells) than NHBEC (normal cells).

Various cell lines are investigated to ascertain whether RBT1 has relevance to carcinogenesis. In silico analysis also suggests that the N-terminal domain of RBT1 contains a putative DNA binding domain. Whether RBT1 binds specific DNA regulatory elements is also being investigated.

The presence of an acidic domain in the C-terminal domain of RBT1 led to investigate whether RBT1 was a potential transcriptional activator. RBT1, fused to the LexA binding domain, strongly promotes transcription of reporter genes LacZ and HIS3 in the yeast two-hybrid system, suggesting its possible role as a transcriptional activator.

RBT1 deletion constructs were designed to determine the transactivating domain, and to define the domain which is essential for RPA32 interaction. The transactivation domain of RBT1 resides within 30 amino acids at the C-terminal. Truncation of RBT1 from the C-terminal end results in significant reduction of transactivation of the reporter genes.

A mammalian transactivation assay confirmed that a GAL4-RBT1 fusion protein indeed acts as a strong transcriptional activator. Furthermore, transcriptional activation, as assayed by a luciferase reporter gene, although high in all cancer cell lines examined, is at least 4 times higher in cell line MCF7. Transactivation studies were also performed using a mammalian system to verify that RBT1 acts as a transcriptional activator in its native cellular environment. RBT1, fused to a GAL4 DNA binding domain, strongly promotes transcription of of B-gal activity with just 60 bp deleted from the 3', suggesting that the potential transcriptional activation domain of RBT1 lies at the carboxy terminal.

Similar constructs may be cloned into a vector for transfection into human cells, using an in-frame fusion to GAL4 DNA-binding domain and utilizing a second plasmid bearing a luciferase reporter gene under the control of several GAL4 binding sites. These experiments determine whether the transactivation found in the yeast system are physiologicallly relevant.

RBT1 may be overexpressed in various human cell lines to ascertain possible phenotypic effects. Experiments may include UV and chemical challenge.

Antibodies against RBT1 may be raised for subsequent protein localization experiments in human cells. This antibody may also be used for various co-immunoprecipitation experiments to show RPA-RBT1 binding.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An isolated nucleotide sequence encoding a protein having the amino acid sequence as set forth in SEQ ID NO: 2.

2. An isolated protein having the amino acid sequence as set forth in SEQ ID NO: 2.

3. A method for increasing the in vitro transcription of a gene, the method comprising introducing the gene operably linked to the isolated nucleotide sequence according to claim 1 into a cell in vitro, expressing the sequence to produce a transcriptional activator protein, thereby increasing the transcription of the gene.

4. The isolated or recombinant nucleotide sequence according to claim 1, said isolated nucleotide sequence having the nucleotide sequence as set forth in SEQ ID NO: 1.

* * * * *

SEQUENCE LISTING

<160> NUMBER OF SEQ ID NOS: 2

<210> SEQ ID NO 1
<211> LENGTH: 591
<212> TYPE: DNA
<213> ORGANISM: Homo sapiens
<220> FEATURE:
<223> OTHER INFORMATION: replication protein A transcriptional factor

<400> SEQUENCE: 1

```
atggagggag gcttgaagag gaaacactct gatttggaag aggaggagga gaggtgggag        60
tggagtccag caggccttca gagctaccag caagccctgc tccgcatctc cctagacaaa       120
gtccagcgca gcctgggccc ccgagcaccc agcctccgca ggcatgtcct catccataac       180
accctccaac agctgcaggc tgcacttcgc ctggctcccg ccctgccct gccccccgag        240
cccctcttcc tgggcgagga ggatttctcc ctgtcagcca ccattggctc tatcctcagg       300
gagctggaca cctccatgga tgggactgag cccctcaga atccagtgac tccccttggc        360
ctccagaatg aagtgccacc ccagcctgat ccagtcttct tagaagctct gagctcccgg       420
tacttggggg actctggcct ggatgacttc tttctggaca ttgacacatc tgcggtagaa       480
aaggagcctg cacgggcccc accagagcct cctcacaacc tcttctgtgc cccaggttct       540
tgggagtgga atgaactgga tcacatcatg gaaatcattc tggggtccta a                591
```

<210> SEQ ID NO 2
<211> LENGTH: 196
<212> TYPE: PRT
<213> ORGANISM: Homo sapiens
<220> FEATURE:
<223> OTHER INFORMATION: replication protein A transcriptional factor

<400> SEQUENCE: 2

```
Met Glu Gly Gly Leu Lys Arg Lys His Ser Asp Leu Glu Glu Glu Glu
 1               5                  10                  15

Glu Arg Trp Glu Trp Ser Pro Ala Gly Leu Gln Ser Tyr Gln Gln Ala
             20                  25                  30

Leu Leu Arg Ile Ser Leu Asp Lys Val Gln Arg Ser Leu Gly Pro Arg
         35                  40                  45

Ala Pro Ser Leu Arg Arg His Val Leu Ile His Asn Thr Leu Gln Gln
     50                  55                  60

Leu Gln Ala Ala Leu Arg Leu Ala Pro Ala Pro Ala Leu Pro Pro Glu
 65                  70                  75                  80

Pro Leu Phe Leu Gly Glu Glu Asp Phe Ser Leu Ser Ala Thr Ile Gly
                 85                  90                  95

Ser Ile Leu Arg Glu Leu Asp Thr Ser Met Asp Gly Thr Glu Pro Pro
            100                 105                 110

Gln Asn Pro Val Thr Pro Leu Gly Leu Gln Asn Glu Val Pro Pro Gln
        115                 120                 125

Pro Asp Pro Val Phe Leu Glu Ala Leu Ser Ser Arg Tyr Leu Gly Asp
    130                 135                 140

Ser Gly Leu Asp Asp Phe Phe Leu Asp Ile Asp Thr Ser Ala Val Glu
145                 150                 155                 160

Lys Glu Pro Ala Arg Ala Pro Pro Glu Pro Pro His Asn Leu Phe Cys
                165                 170                 175
```

```
Ala Pro Gly Ser Trp Glu Trp Asn Glu Leu Asp His Ile Met Glu Ile
            180                 185                 190

Ile Leu Gly Ser
        195
```